United States Patent
Gauthier et al.

(10) Patent No.: US 10,588,642 B2
(45) Date of Patent: Mar. 17, 2020

(54) MOLDING PROCESS AND PRODUCTS FORMED THEREBY

(71) Applicant: Gauthier Biomedical, Inc., Grafton, WI (US)

(72) Inventors: Michael T. Gauthier, Grafton, WI (US); Kenneth A. Roggow, Milwaukee, WI (US)

(73) Assignee: Gauthier Biomedical, Inc., Grafton, WI (US)

( * ) Notice: Subject to any disclaimer, the term of this patent is extended or adjusted under 35 U.S.C. 154(b) by 292 days.

(21) Appl. No.: 14/713,367

(22) Filed: May 15, 2015

(65) Prior Publication Data
US 2016/0007976 A1    Jan. 14, 2016

Related U.S. Application Data

(60) Provisional application No. 61/993,383, filed on May 15, 2014.

(51) Int. Cl.
*A61B 17/16* (2006.01)
*B29C 45/14* (2006.01)
(Continued)

(52) U.S. Cl.
CPC .......... *A61B 17/1631* (2013.01); *A61B 17/00* (2013.01); *A61B 17/1642* (2013.01);
(Continued)

(58) Field of Classification Search
None
See application file for complete search history.

(56) References Cited

U.S. PATENT DOCUMENTS 1,813,797 A * 7/1931 Foley .................... B29C 43/003
                                                     264/247
1,831,752 A * 11/1931 Reinold .................. A47J 45/08
                                                    16/DIG. 30
(Continued)

FOREIGN PATENT DOCUMENTS

CN       2494172 Y  *  6/2002
CN       1357444 A  *  7/2002  ......... A61B 17/3213
(Continued)

OTHER PUBLICATIONS

Gauthier Medical, Silicone Rod Templates, Mar. 2012.*
(Continued)

*Primary Examiner* — Jeffrey A Vonch
(74) *Attorney, Agent, or Firm* — Boyle Fredrickson, S.C.

(57) ABSTRACT

A reusable surgical implement is provided that is formed of a core positioned within an enclosure. The core is formed of a suitable rigid, and optionally flexible material to enable the implant to conform to the desired use for the implement in a surgical procedure. The material forming the enclosure is also stretchable and flexible to accommodate the configuration and/or any flexing of the core, and is biologically inert to enable the implant to be sterilized after use for use in subsequent surgical procedures while protecting the material forming the core. The enclosure can be molded around the core in separate portions or components using multiple molding steps to form an enclosure with the desired attributes.

14 Claims, 2 Drawing Sheets

(51) Int. Cl.

| | | |
|---|---|---|
| *B29C 45/16* | (2006.01) | |
| *B32B 1/04* | (2006.01) | |
| *B32B 3/02* | (2006.01) | |
| *A61B 17/00* | (2006.01) | |
| *A61B 17/88* | (2006.01) | |
| *B29K 83/00* | (2006.01) | |
| *B29K 705/08* | (2006.01) | |
| *B29L 9/00* | (2006.01) | |
| *B29L 31/00* | (2006.01) | |
| *A61B 90/00* | (2016.01) | |
| *A61B 17/70* | (2006.01) | |
| *B29C 45/26* | (2006.01) | |
| *B29L 31/06* | (2006.01) | |
| *B32B 7/02* | (2019.01) | |
| *B32B 15/06* | (2006.01) | |
| *B32B 7/04* | (2019.01) | |
| *B32B 3/30* | (2006.01) | |
| *B32B 3/26* | (2006.01) | |

(52) U.S. Cl.
CPC ........ *A61B 17/88* (2013.01); *B29C 45/14008* (2013.01); *B29C 45/14336* (2013.01); *B29C 45/1671* (2013.01); *B32B 3/02* (2013.01); *A61B 17/164* (2013.01); *A61B 17/1671* (2013.01); *A61B 17/7002* (2013.01); *A61B 17/7029* (2013.01); *A61B 17/7031* (2013.01); *A61B 2017/00526* (2013.01); *A61B 2017/00831* (2013.01); *A61B 2017/00862* (2013.01); *A61B 2017/00867* (2013.01); *A61B 2017/00946* (2013.01); *A61B 2017/00955* (2013.01); *A61B 2017/00964* (2013.01); *A61B 2090/0813* (2016.02); *B29C 45/14549* (2013.01); *B29C 45/14598* (2013.01); *B29C 45/1642* (2013.01); *B29C 45/1679* (2013.01); *B29C 45/261* (2013.01); *B29C 2045/1486* (2013.01); *B29C 2045/14139* (2013.01); *B29K 2083/00* (2013.01); *B29K 2083/005* (2013.01); *B29K 2705/08* (2013.01); *B29L 2009/00* (2013.01); *B29L 2009/003* (2013.01); *B29L 2031/06* (2013.01); *B29L 2031/75* (2013.01); *B29L 2031/7546* (2013.01); *B32B 1/04* (2013.01); *B32B 3/263* (2013.01); *B32B 3/30* (2013.01); *B32B 7/02* (2013.01); *B32B 7/04* (2013.01); *B32B 15/06* (2013.01); *B32B 2311/00* (2013.01); *B32B 2311/005* (2013.01); *B32B 2383/00* (2013.01); *B32B 2535/00* (2013.01)

(56) References Cited

U.S. PATENT DOCUMENTS

| | | | | |
|---|---|---|---|---|
| 2,062,880 A * | 12/1936 | Hansen | ............... | B29C 39/12 264/247 |
| 2,125,783 A * | 8/1938 | Heeman | ............... | E05B 1/0061 292/347 |
| 2,207,269 A * | 7/1940 | Schiff | ............... | B26B 19/3806 30/34.05 |
| 2,256,769 A * | 9/1941 | Amrine | ............... | B29C 33/123 425/116 |
| 2,358,259 A * | 9/1944 | Siedschlag | ............... | B29C 33/126 264/247 |
| 3,259,680 A * | 7/1966 | Schelke | ............... | B29C 45/14065 264/275 |
| 3,913,586 A * | 10/1975 | Baumgarten | ............... | A61B 17/2812 30/254 |
| 4,117,791 A * | 10/1978 | Current | ............... | D05B 85/12 112/222 |
| 4,147,443 A * | 4/1979 | Skobel | ............... | A61B 17/2841 30/343 |
| 4,170,990 A * | 10/1979 | Baumgart | ............... | A61B 17/0644 606/62 |
| 4,318,879 A * | 3/1982 | Gartner | ............... | B29C 45/14073 264/163 |
| 4,340,990 A * | 7/1982 | Seynhaeve | ............... | A45C 13/26 16/445 |
| 4,448,741 A * | 5/1984 | Schad | ............... | B29C 45/162 264/251 |
| 4,469,483 A * | 9/1984 | Becker | ............... | A61M 25/0108 128/DIG. 21 |
| 4,535,014 A * | 8/1985 | Wright | ............... | A46B 5/00 15/167.1 |
| 4,662,404 A * | 5/1987 | LeVeen | ............... | A61M 39/08 138/120 |
| 4,690,175 A * | 9/1987 | Ouchi | ............... | A61B 1/0055 138/131 |
| 4,706,659 A * | 11/1987 | Matthews | ............... | A61B 17/164 464/173 |
| 4,739,536 A * | 4/1988 | Bandera | ............... | B25G 1/10 16/430 |
| 4,750,877 A * | 6/1988 | McFarlane | ............... | B29C 45/261 249/125 |
| 4,751,922 A * | 6/1988 | DiPietropolo | ............... | B23Q 5/043 606/80 |
| 4,799,474 A * | 1/1989 | Ueda | ............... | A61B 1/0058 600/133 |
| 4,867,174 A * | 9/1989 | Skribiski | ............... | A61L 31/06 600/585 |
| 4,882,867 A * | 11/1989 | Linden | ............... | A61C 3/10 40/625 |
| 4,919,133 A * | 4/1990 | Chiang | ............... | A61B 17/320783 606/159 |
| 4,934,024 A * | 6/1990 | Sexton, I | ............... | A63B 49/08 16/421 |
| 4,955,889 A * | 9/1990 | Van Gent | ............... | A61F 2/1664 606/107 |
| 4,959,067 A * | 9/1990 | Muller | ............... | A61B 17/00 600/201 |
| 4,983,168 A * | 1/1991 | Moorehead | ............... | A61M 25/0668 604/161 |
| 5,027,511 A * | 7/1991 | Miller | ............... | B26B 21/522 30/526 |
| 5,069,226 A * | 12/1991 | Yamauchi | ............... | A61L 31/022 600/585 |
| 5,089,201 A * | 2/1992 | Takahashi | ............... | B29C 33/0044 156/287 |
| 5,095,915 A * | 3/1992 | Engelson | ............... | A61M 25/09 600/434 |
| 5,163,431 A * | 11/1992 | Griep | ............... | A61M 25/0041 600/435 |
| 5,222,949 A * | 6/1993 | Kaldany | ............... | A61L 29/06 604/524 |
| 5,230,348 A * | 7/1993 | Ishibe | ............... | A61M 25/09 600/585 |
| 5,334,168 A * | 8/1994 | Hemmer | ............... | A61M 25/0158 604/531 |
| 5,385,152 A * | 1/1995 | Abele | ............... | A61B 17/22 600/434 |
| 5,433,200 A * | 7/1995 | Fleischhacker, Jr. | ............... | A61M 25/09 600/434 |
| 5,498,158 A * | 3/1996 | Wong | ............... | A61C 5/40 433/102 |
| 5,499,984 A * | 3/1996 | Steiner | ............... | A61B 17/164 408/713 |
| 5,533,985 A * | 7/1996 | Wang | ............... | A61M 25/0009 604/264 |
| 5,538,512 A * | 7/1996 | Zenzon | ............... | A61L 29/041 604/264 |
| 5,569,218 A * | 10/1996 | Berg | ............... | A61M 25/0009 138/134 |
| 5,573,529 A * | 11/1996 | Haak | ............... | A61B 90/90 128/898 |

(56) References Cited

U.S. PATENT DOCUMENTS

| | | | | |
|---|---|---|---|---|
| 5,601,003 A * | 2/1997 | Amtenbrink | B25G 1/105 | 81/177.1 |
| 5,662,621 A * | 9/1997 | Lafontaine | A61M 25/0041 | 604/164.13 |
| 5,769,506 A * | 6/1998 | Boucherie | A46D 3/00 | 300/2 |
| 5,772,609 A * | 6/1998 | Nguyen | A61M 25/09 | 600/585 |
| 5,799,369 A * | 9/1998 | Schulein | A47J 45/06 | 16/430 |
| 5,816,806 A * | 10/1998 | Herbst | A61C 3/00 | 433/141 |
| 5,816,923 A * | 10/1998 | Milo | A61B 17/320758 | 464/58 |
| 5,911,715 A * | 6/1999 | Berg | A61M 25/0009 | 138/125 |
| 5,921,978 A * | 7/1999 | Thompson | A61M 25/0108 | 604/523 |
| 5,956,799 A * | 9/1999 | Panaccione | A47L 13/022 | 15/143.1 |
| 5,964,770 A * | 10/1999 | Flomenblit | A61B 17/68 | 604/530 |
| 6,036,682 A * | 3/2000 | Lange | A61M 25/0108 | 604/264 |
| 6,094,781 A * | 8/2000 | Jansson | B25G 1/105 | 16/431 |
| 6,199,460 B1 * | 3/2001 | Lo | B25G 1/10 | 81/177.1 |
| 6,221,077 B1 * | 4/2001 | Rinner | A61B 17/8863 | 33/512 |
| 6,340,441 B1 * | 1/2002 | Meyer | A61M 25/09 | 264/173.12 |
| 6,367,125 B1 * | 4/2002 | Lin | B25G 1/063 | 16/436 |
| 6,402,706 B2 * | 6/2002 | Richardson | A61M 25/09 | 600/585 |
| 6,405,619 B1 * | 6/2002 | Lamond | B25G 3/18 | 16/110.1 |
| 6,494,847 B1 * | 12/2002 | Richardson | A61M 25/09 | 600/585 |
| 6,494,894 B2 * | 12/2002 | Mirarchi | A61M 25/09 | 604/94.01 |
| 6,524,301 B1 * | 2/2003 | Wilson | A61M 25/09 | 604/523 |
| 6,556,873 B1 * | 4/2003 | Smits | A61N 1/0563 | 607/122 |
| 6,591,472 B1 * | 7/2003 | Noone | A61M 25/0009 | 264/171.13 |
| 6,648,024 B2 * | 11/2003 | Wang | B29C 48/49 | 138/177 |
| 6,749,790 B1 * | 6/2004 | Lieser | B25G 1/105 | 16/436 |
| 6,779,937 B1 * | 8/2004 | Lombardi | A45D 40/205 | 401/6 |
| 6,887,417 B1 * | 5/2005 | Gawreluk | A61M 25/0009 | 264/328.1 |
| 6,915,570 B1 * | 7/2005 | Ohgoshi | B29C 45/0001 | 264/262 |
| 7,097,624 B2 * | 8/2006 | Campion | A61M 25/09 | 600/585 |
| 7,651,578 B2 * | 1/2010 | Sharrow | A61M 25/09 | 156/198 |
| 7,780,611 B2 * | 8/2010 | Griego | A61M 25/09 | 600/585 |
| 9,050,062 B1 * | 6/2015 | Gauthier | B25G 1/10 | |
| 9,943,988 B1 * | 4/2018 | Gauthier | A61F 2/4684 | |
| 2001/0041881 A1 * | 11/2001 | Sarge | A61M 25/005 | 604/525 |
| 2002/0013511 A1 * | 1/2002 | Ailinger | A61B 1/0011 | 600/121 |
| 2002/0058928 A1 * | 5/2002 | Antonio, II | A61M 5/1407 | 604/523 |
| 2002/0107088 A1 * | 8/2002 | Lamkin | A63B 60/00 | 473/300 |
| 2002/0128658 A1 * | 9/2002 | White | B23B 31/117 | 606/80 |
| 2002/0165549 A1 * | 11/2002 | Owusu-Akyaw | A61B 17/1628 | 606/80 |
| 2002/0171208 A1 * | 11/2002 | Lechot | B23B 31/117 | 279/9.1 |
| 2002/0190430 A1 * | 12/2002 | Fujiwara | B29C 45/14065 | 264/279 |
| 2003/0097133 A1 * | 5/2003 | Green | A61B 17/1617 | 606/80 |
| 2003/0126750 A1 * | 7/2003 | Spinelli | A47G 21/04 | 30/324 |
| 2003/0176868 A1 * | 9/2003 | Pepper | A61B 17/164 | 606/80 |
| 2003/0229298 A1 * | 12/2003 | Iwami | A61M 25/09 | 600/585 |
| 2004/0097831 A1 * | 5/2004 | Bourne | A61B 10/0266 | 600/564 |
| 2004/0098006 A1 * | 5/2004 | Nakanishi | A61B 17/1631 | 606/170 |
| 2004/0105069 A1 * | 6/2004 | Fecteau | G02C 5/00 | 351/111 |
| 2004/0134028 A1 * | 7/2004 | Chen | B25G 1/10 | 16/110.1 |
| 2004/0167437 A1 * | 8/2004 | Sharrow | A61M 25/09 | 600/585 |
| 2004/0193104 A1 * | 9/2004 | Jervis | A61B 1/32 | 604/44 |
| 2004/0243102 A1 * | 12/2004 | Berg | A61M 25/0013 | 604/525 |
| 2005/0004556 A1 * | 1/2005 | Pursley | A61M 25/0012 | 604/529 |
| 2005/0049623 A1 * | 3/2005 | Moore | A61B 17/1604 | 606/170 |
| 2005/0054953 A1 * | 3/2005 | Ryan | A61M 25/09 | 600/585 |
| 2005/0113686 A1 * | 5/2005 | Peckham | A61F 2/06 | 600/431 |
| 2005/0124991 A1 * | 6/2005 | Jahng | A61B 17/1757 | 606/254 |
| 2005/0137600 A1 * | 6/2005 | Jacobs | A61B 17/1615 | 606/79 |
| 2005/0253301 A1 * | 11/2005 | Kraenzle | B05C 17/00516 | 264/328.1 |
| 2006/0004371 A1 * | 1/2006 | Williams | A61B 17/1615 | 606/80 |
| 2006/0009140 A1 * | 1/2006 | Sommers | A61B 1/247 | 451/523 |
| 2006/0063130 A1 * | 3/2006 | Hayman | A61C 1/07 | 433/141 |
| 2006/0084032 A1 * | 4/2006 | Tipton | A61C 3/00 | 433/141 |
| 2006/0100687 A1 * | 5/2006 | Fahey | A61F 2/95 | 623/1.11 |
| 2006/0110704 A1 * | 5/2006 | Bills | A61C 1/082 | 433/102 |
| 2006/0189897 A1 * | 8/2006 | Poncet | A61M 25/0045 | 600/585 |
| 2006/0199994 A1 * | 9/2006 | Inman | A61B 17/0401 | 600/30 |
| 2006/0247638 A1 * | 11/2006 | Trieu | A61B 17/7031 | 606/246 |
| 2006/0264935 A1 * | 11/2006 | White | A61B 17/7031 | 606/257 |
| 2007/0003903 A1 * | 1/2007 | Meuchel | A61C 3/00 | 433/141 |
| 2007/0049937 A1 * | 3/2007 | Matthis | A61B 17/702 | 606/254 |
| 2007/0073312 A1 * | 3/2007 | Mykleby | A61M 1/008 | 606/113 |
| 2007/0123826 A1 * | 5/2007 | Opie | A61B 17/00008 | 604/164.13 |

(56) References Cited

U.S. PATENT DOCUMENTS

| | | | |
|---|---|---|---|
| 2007/0153229 A1* | 7/2007 | Yasuhara | G02C 5/143 351/122 |
| 2007/0161427 A1* | 7/2007 | White | F16C 1/02 464/52 |
| 2007/0191841 A1* | 8/2007 | Justis | A61B 17/701 606/250 |
| 2007/0299366 A1* | 12/2007 | Sharrow | A61M 25/09 600/585 |
| 2008/0125238 A1* | 5/2008 | Chen | A63B 53/14 473/300 |
| 2008/0125777 A1* | 5/2008 | Veldman | A61B 17/7029 606/264 |
| 2008/0140022 A1* | 6/2008 | Pond | A61M 25/065 604/272 |
| 2008/0146967 A1* | 6/2008 | Richardson | A61L 31/10 600/585 |
| 2008/0177388 A1* | 7/2008 | Patterson | A61B 17/7031 623/17.16 |
| 2008/0234711 A1* | 9/2008 | Houser | A61B 17/320068 606/169 |
| 2008/0243126 A1* | 10/2008 | Gutierrez | A61B 17/1631 606/84 |
| 2008/0255664 A1* | 10/2008 | Hogendijk | A61B 17/562 623/11.11 |
| 2008/0287952 A1* | 11/2008 | Mcminn | A61B 17/1624 606/80 |
| 2008/0290104 A1* | 11/2008 | Ng | A47J 45/061 220/753 |
| 2008/0312597 A1* | 12/2008 | Uihlein | A61M 25/09 604/164.13 |
| 2008/0312654 A1* | 12/2008 | Weatherdon | A61B 90/90 606/53 |
| 2008/0319486 A1* | 12/2008 | Hestad | A61B 17/7031 606/255 |
| 2009/0054932 A1* | 2/2009 | Butler | A61B 17/7013 606/255 |
| 2009/0088750 A1* | 4/2009 | Hushka | A61B 18/1445 606/51 |
| 2009/0088782 A1* | 4/2009 | Moumene | A61B 17/7004 606/151 |
| 2009/0112066 A1* | 4/2009 | Yago | A61B 1/00071 600/140 |
| 2009/0112127 A1* | 4/2009 | Keating | A61M 25/09 600/585 |
| 2009/0161063 A1* | 6/2009 | Parent | G02C 5/18 351/114 |
| 2009/0221935 A1* | 9/2009 | Murayama | A61M 25/09 600/585 |
| 2009/0248080 A1* | 10/2009 | Wilcox | A61B 17/7002 606/261 |
| 2009/0259257 A1* | 10/2009 | Prevost | A61B 17/7011 606/255 |
| 2009/0270922 A1* | 10/2009 | Biedermann | A61B 17/7031 606/262 |
| 2010/0005630 A1* | 1/2010 | Gitman | A61B 17/3213 16/430 |
| 2010/0030256 A1* | 2/2010 | Dubrul | A61B 10/0266 606/200 |
| 2010/0063544 A1* | 3/2010 | Butler | A61B 17/701 606/261 |
| 2010/0063548 A1* | 3/2010 | Wang | A61B 17/7002 606/279 |
| 2010/0102479 A1* | 4/2010 | Walls | A63B 53/14 264/255 |
| 2010/0256601 A1* | 10/2010 | Lippert | A61M 25/0013 604/523 |
| 2010/0256603 A1* | 10/2010 | Lippert | A61M 25/0009 604/524 |
| 2010/0256605 A1* | 10/2010 | Lippert | A61M 25/0009 604/529 |
| 2010/0324577 A1* | 12/2010 | Dunn | A61B 17/3213 606/167 |
| 2011/0071570 A1* | 3/2011 | Trieu | A61B 17/7011 606/254 |
| 2011/0138975 A1* | 6/2011 | Holm | B29C 45/1676 81/489 |
| 2011/0152937 A1* | 6/2011 | Trieu | A61B 17/7026 606/264 |
| 2011/0168419 A1* | 7/2011 | Reynolds | B23B 45/003 173/46 |
| 2011/0218538 A1* | 9/2011 | Sherman | A61B 17/1631 606/80 |
| 2011/0257685 A1* | 10/2011 | Hay | A61B 17/7007 606/263 |
| 2012/0041425 A1* | 2/2012 | Tsunematsu | A61M 39/10 604/535 |
| 2012/0253348 A1* | 10/2012 | Arlettaz | A61B 17/1631 606/80 |
| 2012/0290013 A1* | 11/2012 | Simonson | A61B 17/7004 606/279 |
| 2013/0066164 A1* | 3/2013 | Nakamura | A61B 17/22031 600/247 |
| 2013/0233863 A1* | 9/2013 | Lapine | A47J 45/00 220/573.1 |
| 2013/0253481 A1* | 9/2013 | Dewaele | A61B 1/00071 606/1 |
| 2015/0121708 A1* | 5/2015 | Holm | B26B 23/00 30/340 |
| 2015/0257800 A1* | 9/2015 | Harshman | A61B 17/7208 606/62 |
| 2015/0313755 A1* | 11/2015 | Schaller | A61F 9/007 606/107 |
| 2016/0023504 A1* | 1/2016 | Shapiro | A47G 21/04 30/526 |
| 2016/0184555 A1* | 6/2016 | Ishikawa | A61L 29/04 604/528 |
| 2018/0177532 A1* | 6/2018 | Gauthier | A61B 17/702 |

FOREIGN PATENT DOCUMENTS

| | | | | |
|---|---|---|---|---|
| CN | 200995040 Y | * | 12/2007 | |
| CN | 101954810 A | * | 1/2011 | B25G 1/102 |
| CN | 102188280 A | * | 9/2011 | |
| CN | 102717478 A | * | 10/2012 | B27N 5/00 |
| DE | 7914109 U1 | * | 5/1979 | B29C 45/16 |
| DE | 102006054477 A1 | * | 5/2008 | B25B 15/02 |
| EP | 0904921 A1 | * | 3/1999 | B29C 45/14065 |
| EP | 1561548 A1 | * | 8/2005 | B25G 3/36 |
| FR | 2509986 A1 | * | 1/1983 | A61B 17/866 |
| FR | 2612305 A1 | * | 9/1988 | G02C 5/00 |
| GB | 501019 A | * | 2/1939 | B27N 5/00 |
| GB | 2359268 A | * | 8/2001 | B25G 1/102 |
| GB | 2464751 A | * | 5/2010 | A61B 17/3213 |
| GB | 2493147 A | * | 1/2013 | B25G 1/102 |
| JP | 01086908 A | * | 3/1989 | B29C 45/16 |
| JP | 01115510 U | * | 8/1989 | |
| JP | 2003191681 A | * | 7/2003 | G02C 5/00 |
| JP | 2007037777 A | * | 2/2007 | |
| KR | 20100071574 A | * | 6/2010 | B29C 37/0085 |
| KR | 20100071575 A | * | 6/2010 | |
| WO | WO-2008022524 A1 | * | 2/2008 | A47J 45/00 |
| WO | WO-2011066231 A1 | * | 6/2011 | A61B 17/7011 |

OTHER PUBLICATIONS

Machine Translation of CN2494172Y, Jun. 2002 (Year: 2002).*
Silicone Handles, Gauthier Medical, Feb. 2012 (Year: 2012).*
Hoxha et al., Field-improvised war surgery in Kosovo: use of kitchen utensils as surgical instruments., Jun. 2008, Military Medicine, vol. 173, pp. 529-533 (Year: 2008).*

* cited by examiner

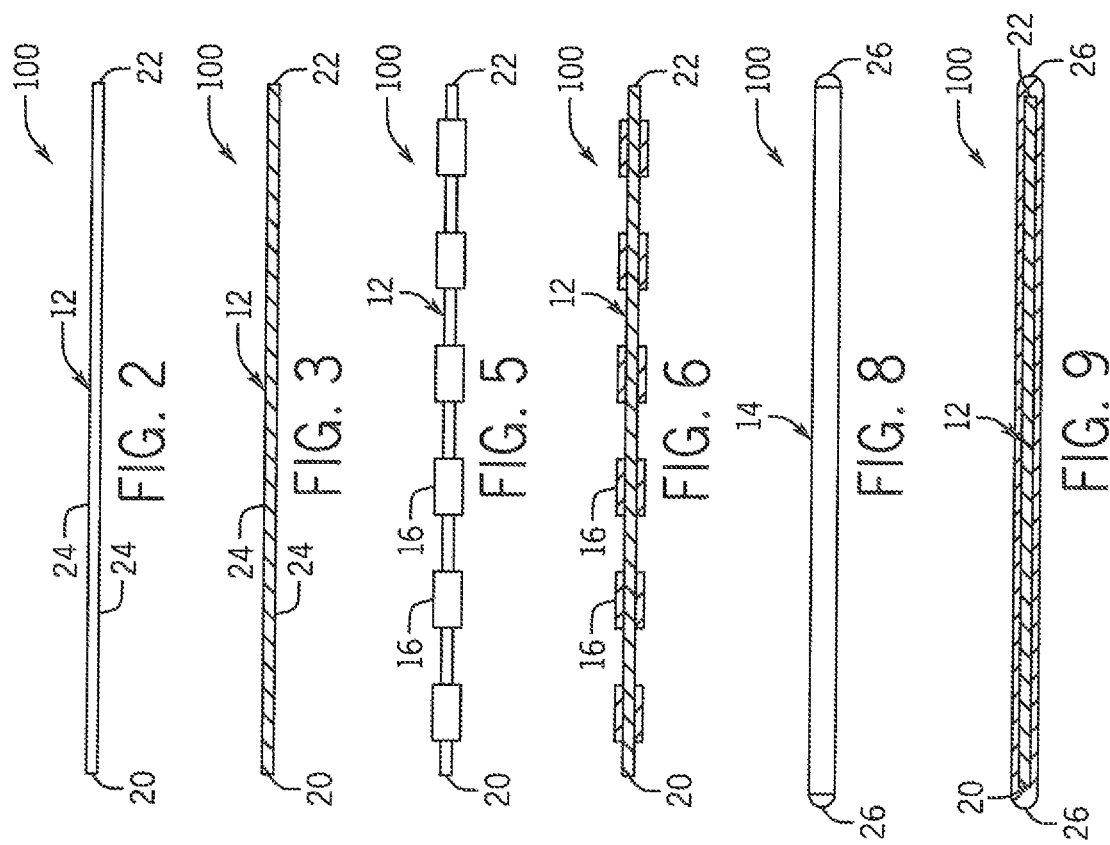
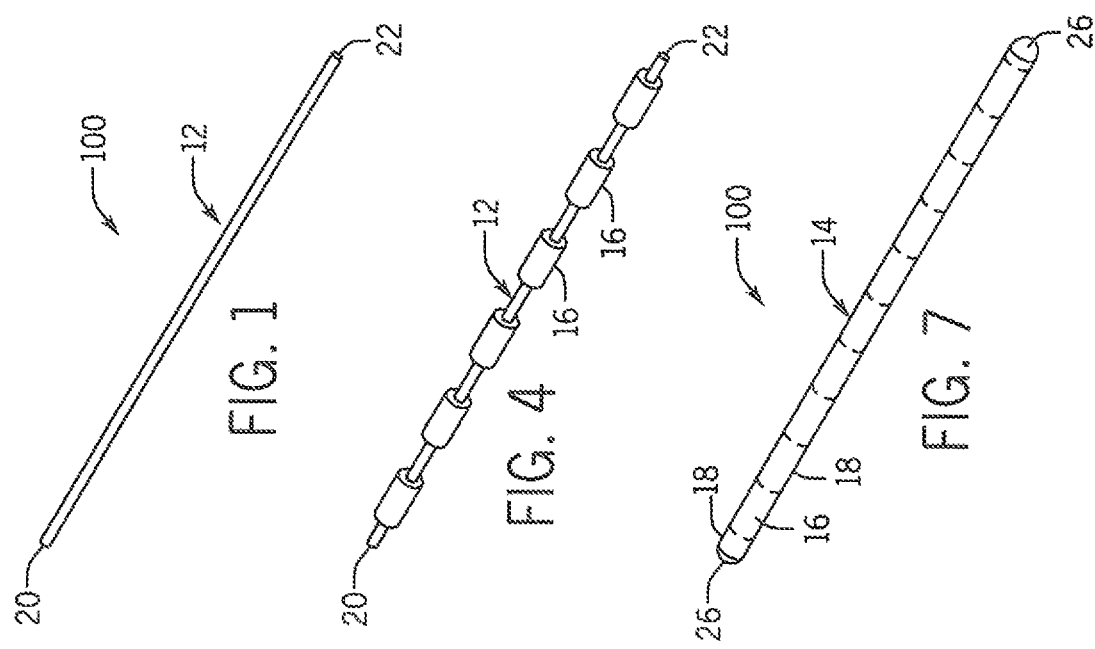

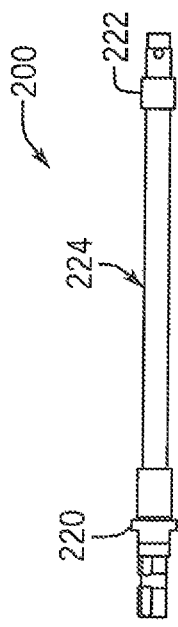
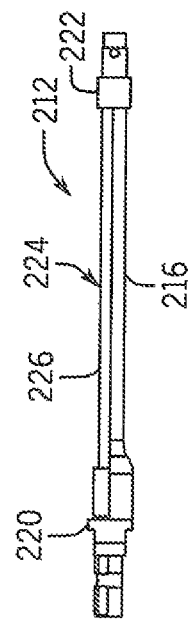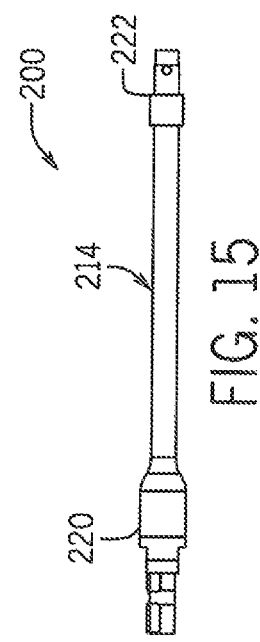
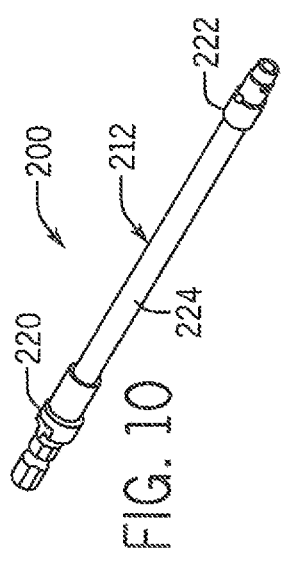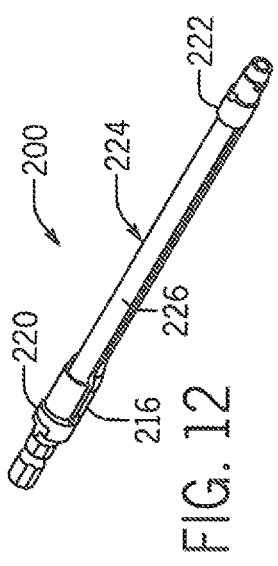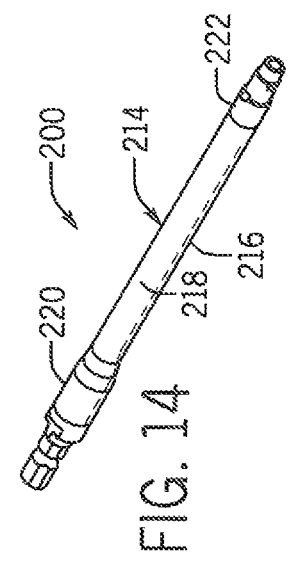

MOLDING PROCESS AND PRODUCTS FORMED THEREBY

CROSS-REFERENCE TO RELATED APPLICATIONS

This application claims priority from U.S. Provisional Patent Application Ser. No. 61/993,383, filed on May 15, 2014, the entirety of which is expressly incorporated herein by reference.

FIELD OF THE INVENTION

The present invention relates generally to items used in surgical procedures, and more particularly to a process for molding exterior coatings on those items and the items formed by the molding process.

BACKGROUND OF THE INVENTION

There are many types of devices that are used in surgical procedures. The devices enable a physician to perform the multitude of tasks required to successfully complete the procedure. Oftentimes, the procedure that the physician needs to perform requires the use of items, implements or other tools that require a certain amount of rigidity in the tool in order for the tool to effective in its particular use in the procedure. As such, many of these items or tools are formed of a generally rigid material, such as a metal, that provides the desired amount of rigidity.

However, with these tools formed at least partially of metal, the nature of the metal creates problems with regard to the re-use of the tool. The reason for this is that the metal, as well as any coating applied to the exterior of the metal, such as an anodized coating which is necessary for implements that are formed of titanium, must be sterilized after each use. With certain metals and coatings, the sterilization process can be problematic, as the metals and/or coating can become brittle or otherwise damaged upon sterilization after an initial use. Any damage done to the metal and/or coating can cause issues with the stability or integrity of the implement during subsequent uses which consequently can endanger the patient.

Thus, it is desirable to develop implements that are formed of metal and a material that enables the implement/tool incorporating the metal to be sterilized and reused in multiple procedures without detrimentally affecting the tool and/or the metal component(s) of the tool.

SUMMARY OF THE INVENTION

Briefly described, one aspect of the present disclosure provides an implement or tool formed of a substantially rigid, but optionally somewhat flexible core material that is enclosed within an inert material. The inert material provide a protective barrier around the core material and is capable of being sterilized after use without degrading the protective properties of the inert material to enable the implement to be reused. The inert material is molded over the core material to conform to the shape of the actual implement to provide the appropriate size and shape for the implement or tool when used by a physician in the procedure. Once used, the implement can be removed and subsequently sterilized, such as in an autoclave, for additional uses.

According to another aspect of the present disclosure, the inert material is flexible and stretchable to accommodate any required flexibility of the core material while maintaining the core enclosed within the inert material. Thus, the implement can be bent in order to accurately conform to the proper location and configuration of for the implement when positioned within the body of the patient during the procedure and the inert material will maintain its conformance with the shape of the core.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings:

FIG. 1 is an isometric view of one embodiment of an implement core constructed according to the present disclosure;

FIG. 2 is a side elevation view of the core of FIG. 1;

FIG. 3 is a cross-sectional view of the core of FIG. 2;

FIG. 4 is an isometric view of the core of FIG. 1 after a first molding step;

FIG. 5 is a side elevation view of the core of FIG. 4;

FIG. 6 is a cross-sectional view of the core of FIG. 5;

FIG. 7 is an isometric view of the core/implement of FIG. 1 after a second molding step;

FIG. 8 is a side elevation view of the core/implement of FIG. 7;

FIG. 9 is a cross-sectional view of the core/implement of FIG. 8;

FIG. 10 is an isometric view of a second embodiment of an implement core constructed according to the present disclosure;

FIG. 11 is a side elevation view of the implement core of FIG. 10;

FIG. 12 is an isometric view of the implement core of FIG. 10 after a first molding step;

FIG. 13 is a side elevation view of the implement core of FIG. 12;

FIG. 14 is an isometric view of the implement core of FIG. 10 after a second molding step;

FIG. 15 is a side elevation view of the implement core of FIG. 14.

DETAILED DESCRIPTION OF THE INVENTION

Referring now in detail to the drawing figures, wherein like reference numerals represent like parts throughout the several views, one exemplary embodiment of an implement constructed according to the present disclosure is illustrated generally at 100 in FIG. 7. As best shown in FIGS. 1-9, the illustrated exemplary embodiment of the implement 100 is formed as a rod template having a central core 12 and an enclosure 14 disposed around the core 12 formed of a first component or portion(s) 16 and a second component or portion(s) 18. In the illustrated exemplary embodiment, the rod template 100 is formed to be generally straight, though other curved, looped or other configurations for the rod template 100 are also contemplated as being within the scope of the disclosure of the present invention.

Though any suitable shape for the core 12 can be utilized, in the illustrated embodiment the core 12 is formed with a generally flat rectangular or cylindrical cross-sectional shape with a first end 20 and a second end 22 joined by opposed sides 24, though any suitable cross-sectional shape can be utilized to impart the desired amount of flexibility to the core 12. The core 12 is shaped in any suitable machine and/or process to provide the desired shape for the core 12, which may include apertures or other features therein, as desired.

The material forming the core 12 is selected to be a generally rigid, but flexible material that can be altered in shape by applying a physical force to the core 12. Once the force is removed, the core 12 remains in the shape to which it was altered by the applied force. In one exemplary embodiment of the core 12, the core 12 is formed of a shape memory material, such as a shape memory metal alloy, including the materials marketed under the trade name Nitinol® by Nitinol Devices & Components, Inc. of Fremont, Calif.

The enclosure 14 is disposed around the core 12 and each portion 16 and 18 joined together to form the enclosure 14 is formed of a biologically inert and flexible material that can conform to the shape of the core 12 in any configuration for the core 12. In one embodiment, the material forming the portions 16 and 18 of the enclosure 14 is a silicone, such as a silicone rubber, including a high consistence rubber (HCR).

The portions 16 and 18 of the enclosure 14 are formed with any features (not shown) desired to enhance the utility of the implement 100 when utilized within the body of the patient. The features can include apertures 110, notches (not shown), raised or depressed tactile portions, or printed indicia, among others. The apertures can extend completely through the respective portions 16 and 18 without intersecting the core 12, thereby preserving the integrity of the enclosure 14 around the core 12. Further, the shape of the portions 16 and 18 forming the enclosure 14 can be shaped as desired. Also, the shape of the portions 16 and 18 can be selected independently of the shape of the core 12 to facilitate the operation or use of the implement 100, or to conform to the shape of the core 12, as desired.

In one embodiment, the implement 100 is formed by initially forming the core 12 of the desired material in any suitable manner, such as by extruding or molding the material into the desired shape for the core 12, as shown in FIGS. 1-3. The core 12 is then placed within a suitable mold (not shown) to enable the material selected to form the first portion 16 to be introduced into the mold containing the core 12 and form a portion of the enclosure 14 on or over the core 12 that contains the desired features within the portion 16. Any suitable molding process can be utilized to form the first portion 16 around the core 12, such as those shown in commonly owned U.S. Pat. No. 8,641,955 and its related applications, each of which are expressly incorporated by reference herein in their entirety. In the illustrated embodiment best shown in FIGS. 4-6, the first portion 16 constitutes a number of spaced sections 102 disposed along the length of the core 12.

Subsequently, the core 12 and the first portion 16 that has been molded onto or over the core 12 are removed or transferred from the first mold and placed within a separate or second mold (not shown) used to form the other of the second portion 18 on or over the core 12 in connection with the first portion 16 and with the desired features. The material selected to form the second portion 18 can be selected to be the same or different in one or more respects or attributes than the material used to form the first portion 16, in order to provide the desired attributes to the enclosure 14 and the implement 100, so long as the materials forming the first portion 16 and second portion 18 are capable of mating, co-mingling or otherwise joining to one another in the molding process used to form the enclosure 14 around the core 12, which can be the same or different that the process used to form the first section 16. Additionally, suitable materials can be applied to one or both of the portions 16 and/or 18 to properly affix the portions 16 and 18 to one another, either during molding of the portions 16 and 18 to one another, or when affixing pre-molded portions 16 and 18 to one another around the core 12.

In alternative exemplary embodiments, the portions 16 and 18 can be formed subsequently or simultaneously within a single mold in any suitable molding process. In the illustrated embodiment, the second portion 18 includes a number of spaced sections 104 disposed along the length of the core 12 and joining the sections 102 to form the enclosure 14. In this embodiment, as shown in FIGS. 7-9, the sections 102 and 104 form a seamless enclosure 14 around the core 12 complete with end caps 106 disposed over each end 20,22 of the core 12. The seamless enclosure 14 moves, stretches and/or flexes with the core 12 to retain the core 12 encased within the enclosure 14, such that the sterilization of the implement 100 does not contact the core 12.

In a second embodiment of the implement 200 shown in FIGS. 10-15 illustrates the implement 200 as a flex driver. The implement 200 includes a suitably shaped core 212 with a pair of opposed ends 220 and 222. The ends 220 and 222 define a central section 224 therebetween, as best shown in FIGS. 10-13. In the embodiment shown in FIGS. 12 and 13, the first portion 216, which can be formed similarly to the first portion 16 in the prior embodiment, is molded onto the core 212 in a first mold (not shown) in a first molding step over at least approximately one half of the central section 224 in a suitable process, such as those cited as examples for the molding of the first portion 16 in the prior embodiment. In this process, however, the ends 220 and 222 can function as stops for the flow of the material forming the first portion 216 at each end 220 and 222.

Subsequently, the core 212 can be removed from the first mold for positioning in a second mold (not shown), or simply rotated within the first mold to expose the uncovered portion 226 of the central section 224 within the second mold. Once properly positioned, the second portion 218 can be formed over the uncovered section 226 to form the enclosure 214 over the central section 224 with the first portion 216 and without end caps, leaving the ends 220,222 exposed.

In alternative exemplary embodiments for either embodiment of the implement 100, 200, the process for molding the first portion 16,216 and/or second portion 18,218 can be performed in any number of separate molding steps in order to form the enclosure 14, 214 on the core 12,212 with the desired appearance, attributes or other characteristics with any desired number and/or types of different materials forming the portions 16,216 and/or 18,218.

Various other embodiments of the present disclosure are contemplated as being within the scope of the filed claims particularly pointing out and distinctly claiming the subject matter regarded as the invention.

The invention claimed is:

1. A flex driver to be used as a surgical implement comprising:
    a) a core; and
    b) an enclosure formed around the core of at least one molded component to completely enclose the portion of the core on which the at least one molded component is disposed, wherein the enclosure is configured for insertion within a body of a patient and is formed of a first portion and a second portion, wherein the first portion and the second portion have flexibility to enable the enclosure to conform to the shape of the core, wherein the core includes a stop at each end that extends radially outwardly from the core around the entire circumference of each end to limit the first portion and the second portion.

2. The flex driver of claim 1, wherein the first portion and the second portion are formed of different materials.

3. The flex driver of claim 2, wherein the first portion and the second portion are mating, co-mingling, or joining to one another to form a seamless enclosure.

4. The flex driver of claim 2, wherein the first portion and the second portion are mirror images of one another and encompass opposed radial halves of the core.

5. The implement flex driver of claim 4, wherein the first portion and the second portion each comprises:
   a narrow section;
   a wide section; and
   a sloped section joining the narrow and wide sections.

6. The flex driver of claim 1, wherein the first portion and second portion are formed from materials selected from the group consisting of silicone, silicone rubber, and high consistency rubber.

7. The flex driver of claim 1, wherein the core is formed of a shape memory material.

8. The flex driver of claim 7, wherein the shape memory material is a shape memory metal alloy.

9. The flex driver of claim 1, wherein the flex driver is sterilizable in an autoclave.

10. A method of forming the flex driver of claim 1, the method comprising the steps of:
   a) forming a the core;
   b) molding a the first component of an the enclosure around the core; and
   c) molding a the second component of an the enclosure around the core in engagement with the first component.

11. The method of claim 10, wherein the step b) comprises placing the core into a mold.

12. The method of claim 11, wherein the step c) comprises removing the core having the first portion thereon and an uncovered section not having the first portion thereon from the mold and positioning it in a second mold, wherein molding the second portion covers the uncovered section.

13. The method of claim 11, wherein the step c) comprises rotating the core having the first portion thereon in the mold to expose an uncovered section not having the first portion thereon, wherein molding the second portion covers the uncovered section.

14. The method of claim 11, wherein the mold is an injection mold.

* * * * *

UNITED STATES PATENT AND TRADEMARK OFFICE
CERTIFICATE OF CORRECTION

PATENT NO. : 10,588,642 B2
APPLICATION NO. : 14/713367
DATED : March 17, 2020
INVENTOR(S) : Michael T. Gauthier et al.

It is certified that error appears in the above-identified patent and that said Letters Patent is hereby corrected as shown below:

In the Claims

Claim 10, Column 6, Line 6, delete "the" first occurrence;

Claim 10, Column 6, Line 6, delete "the" second occurrence;

Claim 10, Column 6, Line 8, delete "the" first occurrence;

Claim 10, Column 6, Line 8, delete "an".

Signed and Sealed this
Ninth Day of June, 2020

Andrei Iancu
*Director of the United States Patent and Trademark Office*